(12) United States Patent
Osipchuk et al.

(10) Patent No.: US 7,056,430 B1
(45) Date of Patent: Jun. 6, 2006

(54) DETACHABLE CELL-DELIVERY SYSTEM FOR PATCH-CLAMP UNIT

(75) Inventors: Yuri Osipchuk, Foster City, CA (US); Yuriy Roll, Foster City, CA (US); Alan S. Finkel, E. Malvern (AU); Alexander A. Dromaretsky, Davis, CA (US); Branko Bem, Newark, CA (US)

(73) Assignee: Axon Instruments, Inc., Union City, CA (US)

( * ) Notice: Subject to any disclaimer, the term of this patent is extended or adjusted under 35 U.S.C. 154(b) by 633 days.

(21) Appl. No.: 10/339,142

(22) Filed: Jan. 9, 2003

Related U.S. Application Data

(60) Provisional application No. 60/347,032, filed on Jan. 9, 2002.

(51) Int. Cl.
*G01N 33/487* (2006.01)
(52) U.S. Cl. .............. 205/777.5; 205/792; 204/403.01; 204/547; 204/643; 435/287.1
(58) Field of Classification Search ........... 204/403.01, 204/547, 643; 205/777.5, 792; 435/7.21, 435/287.1, 288.1
See application file for complete search history.

(56) References Cited

U.S. PATENT DOCUMENTS

| | | | | |
|---|---|---|---|---|
| 5,154,814 | A | * 10/1992 | Kawamura et al. | ......... 204/643 |
| 6,284,113 | B1 | * 9/2001 | Bjornson et al. | ........... 204/453 |
| 6,482,619 | B1 | * 11/2002 | Rubinsky et al. | ........ 435/173.7 |
| 6,492,175 | B1 | 12/2002 | Miller et al. | |
| 2002/0144905 | A1 | 10/2002 | Schmidt | |
| 2002/0182627 | A1 | 12/2002 | Wang et al. | |

FOREIGN PATENT DOCUMENTS

WO PCT/IB98/01150 7/1998

OTHER PUBLICATIONS

Evotek Technologies, "CYTOMAN Touch-Free Cell Manipulation," brochure, month, year unknown.
Evotek Technologies, "CYTOMAN Effect of Drugs on Intracellular Surfactant Transport Processes in Single Living Type II Pneumocytes," brochure, month, year unknown.
Evotek Technologies, "CYTOMAN Calibration of Infrared Laser Tolerance of Cells," brochure, month, year unknown.
Evotek Technologies, "CYTOMAN 3D Microscopy of Suspended Cells," brochure, month, year unknown.
Evotek Technologies, "CYTOMAN See What You Get Processing Cells Under Microscope Control," brochure, month, year unknown.

(Continued)

*Primary Examiner*—Kaj K. Olsen
(74) *Attorney, Agent, or Firm*—Antonio R. Durando

(57) ABSTRACT

The cell-delivery unit of a high-throughput electrophysiological testing system is implemented as a reusable movable unit suitable for repetitive delivery of cells to a disposable, multi-aperture patch-clamp tray. An electric field emanating from the patch aperture is used to align the dispenser with the aperture. A set of electrodes in the nozzle of the dispenser is used to detect the electric field and effect the alignment. According to another aspect of the invention, dielectrophoretic fields produced by sets of electrodes in the nozzle form a retaining cage that is used first to suspend a test cell directly above the patch aperture and then to urge the cell toward it. A movable cell sorter may also be coupled to the cell-delivery unit.

19 Claims, 13 Drawing Sheets

OTHER PUBLICATIONS

Evotek Technologies, "CYTOMAN Multivalent Receptor Ligand Interaction Measured on Single Cells," brochure, month, year unknown.

Evotek Technologies, "CYTOCON 300 One-Step Analysis and Picking of CHO Clones Carrying Endothelin Receptors," brochure, month, year unknown.

Evotek Technologies, "CYTOCON 300 Sorting of Small Cell Populations," brochure, month, year unknown.

Evotek Technologies, "CYTOCON 300 Kinetic Analysis of Single Cells," brochure, month, year unknown.

Evotek Technologies, "CYTOCON 300 Fractionation of Blood Cells," brochure, month, year unknown.

Evotek Technologies, "CYTOCON 300 See What You Get Processing Cells Under Microscope Control," brochure, month, year unknown.

* cited by examiner

DETACHABLE CELL-DELIVERY SYSTEM FOR PATCH-CLAMP UNIT

RELATED APPLICATIONS

This application is based on U.S. Provisional Application Ser. No. 60/347,032, filed on Jan. 9, 2002.

BACKGROUND OF THE INVENTION

1. Field of the Invention

This invention is related in general to electrodes for electrophysiological testing of biological membranes and, in particular, to a cell-delivery unit that is especially suitable for massive parallel testing of cells. The invention includes a reusable cell-delivery component that is separable from the patch-clamp component of the electrode assembly, a method for automatically aligning the two components rapidly and reliably using electric-field probing, and a method for positioning test cells accurately on the patch aperture using dielectrophoresis.

2. Description of the Related Art

In conventional patch clamping used to conduct electrophysiological tests on membranes, a micropipette with a heat-polished tip of about 1 to 5 μm in diameter is physically sealed to a "patch" on the membrane. The electrical activity in the membrane is then assessed by measuring current or voltage changes produced in response to exposure to various test stimuli, such as voltage step changes, current injection, the application of compounds, or mechanical stimulation. Typically, the membrane potential is controlled while the current flowing through the membrane is measured to detect ion-channel activity that corresponds to changes in the membrane's conductance.

For the most part, patch clamping is used either in a whole-cell or a single-channel mode of operation. In whole-cell patch clamping, the membrane at the tip of the pipette is ruptured to produce electrical continuity between the electrolyte in the pipette and the interior of the cell. Thus, total membrane current or voltage is measured. In single-channel patch clamping, the integrity of the membrane at the tip of the pipette is preserved. Accordingly, the recorded current is only the current flowing through the patch of the membrane enclosed by the tip of the pipette. Since this area is very small, there is a good chance that only one or a small number of ion channels may be in the membrane patch, and individual ion-channel currents may be recorded.

In both types of patch-clamp techniques, when the tip of the pipette is pressed against the cell membrane, the interior of the pipette is isolated from the extracellular solution by the seal that is formed between the tip of the pipette and the membrane. If the electrical resistance of the seal is very high (in the order of several hundred mega-ohm to several giga-ohms), no current can leak across the seal and good measurements are obtained. Thus, any leakage of current through the seal is undesirable and the creation of a high-resistance seal (in the order of giga-ohms) is crucial for good results.

New planar patch-clamp electrodes have been developed in the art based on a seal formed by a test cell's membrane and an aperture in a nonconductive partition separating the extracellular carrier solution from an intracellular electrolyte. Typically, these systems comprise multiple perfusion chambers where the partition separates a top (extracellular) compartment, where the test cells are suspended in an extracellular solution, from a bottom (intracellular) compartment containing an electrode and an intracellular solution. The plate configuration of the partition allows the manufacture of a disposable tray with multiple perfusion chambers for parallel testing of large numbers of cells. For instance, International Application No. PCT/IB98/01150 describes a perforated partition with multiple holes for forming a plurality of patch-clamp seals between intra and extracellular compartments.

Patch clamp requires placing a test cell onto the aperture connecting the two compartments of each chamber. Thus, a planar partition between intracellular and extracellular compartments provides a patch-clamp aperture (often also called "pore" in the art) in each perfusion chamber. The dimension of a typical aperture is about 2 micron and the precise positioning of a test cell over the aperture is a critical factor for the speed of operation of a patch-clamp system. In conventional (manual) patch clamp, the cell is brought into contact with the aperture (which in that case is the pore in the tip of a patch pipette) by manipulating the pipette under microscopic control by a skilled operator. Obviously, high-throughput electrophysiology cannot be accomplished by this process and requires an approach suitable for automation.

High-throughput systems described in the art incorporate the cell-positioning compartment and the patch-clamp compartment into a single structure, typically implemented in "chip" format. One such system is described, for example, in U.S. Patent Application No. 2002/0182627. For successful operation, the test cell needs to be placed in the immediate vicinity of the patch pore in each perfusion chamber, preferably within a few microns from the pore, with subsequent application of solution suction through the pore to bring the cell directly into the pore. In the case of a planar patch, the pore is an aperture in an essentially flat, electrically insulating substrate separating the two compartments. Several ways have bee proposed for accomplishing this initial positioning of the test cells in an automated system, such as using microfluidics to create solution flow in the vicinity of the pore that brings the cell to the pore (disclosed in commonly owned U.S. Ser. No. 09/973,388, herein incorporated by reference), and using voltage applied across the pore to create electric fields in the solution which attract the cell to the pore by dielectrophoretic forces (as described, for example, in International Application No. PCT/IB98/01150 and U.S. Publication No. 2002/0144905). In practice, microfluidics flow requires complicated and expensive channels in the vicinity of the pore.

Thus, in addition to the ability to form a high-resistance seal, high-throughput electrophysiological testing requires a reliable and practical approach to the challenge of accomplishing the initial positioning of test cells in the vicinity of the patch-clamp apertures. Furthermore, inasmuch as disposable patch-clamp partitions need to be replaced between tests, the single-structure construction of high-throughput electrophysiological perfusion apparatus adopted in the art greatly contributes to the high cost of operating these systems. This invention provides a different approach that substantially improves these problems.

BRIEF SUMMARY OF THE INVENTION

According to one aspect of the invention, the patch-clamp section of a high-throughput electrophysiological testing system is separated from the cell delivery system. The patch aperture in the nonconductive partition can be used only once; therefore, this substrate is necessarily a disposable component of the apparatus. Thus, in order to reduce the overall cost of high-throughput testing, the cell-delivery system of the invention is implemented as a reusable unit suitable for repetitive, sequential coupling with a separate, disposable, patch-clamp section.

The adoption of this approach for high-throughput operation requires the ability to rapidly and precisely align the patch-clamp and the cell-delivery sections in an automated fashion. It is virtually impossible to engineer a system with detachable components that can be assembled rapidly with sufficient accuracy (in the order of a few microns) to ensure the proper alignment of each patch pore with the nozzle of a cell-delivery unit. Standard machining and plastic-injection molding tolerances of patch-clamp partitions are not precise enough to guarantee that the exact position of each aperture in the disposable section is known. Therefore, according to the invention, electric-field signals are used to align the reusable cell-delivery unit with the disposable patch-aperture section of the test assembly.

The nozzle of the cell-delivery unit (consisting essentially of a tube) is equipped with a set of electrodes preferably disposed uniformly with respect to the center of the nozzle on a plane normal to the nozzle's longitudinal axis. The electrodes are connected to sensitive amplifiers by conductors embedded in the structure of the unit. As the cell-delivery unit is moved automatically toward a patch-clamp aperture, a voltage potential is applied to create an electric field between the intracellular and the extracellular compartments, the highest field being in the proximity of the aperture. Initially, the cell-delivery unit is brought into close proximity of the patch aperture using a mechanical positioner and the coordinates of the aperture, which produces an alignment limited by mechanical tolerances and the inexact knowledge of the position of the aperture. As the two parts are brought into proximity, the electrodes are used to measure the potential at different points of known location in the extracellular compartment. Because the electric field in the extracellular compartment emanates from the patch aperture, the potential of all electrodes will be equal when the nozzle of the cell-delivery unit is centered over the patch aperture. Thus, an active "hole-seeking" mechanism for aligning the cell-delivery unit to the patch-clamp aperture can be implemented automatically using a computer-controlled actuator connected to the electrodes and a feedback loop adapted to minimize the voltage difference between electrodes.

After the cell-delivery unit is so aligned with the patch aperture of interest, an electric voltage suitable to create a dielectrophoretic field is applied between the electrodes in the cell-delivery unit. The same electrodes used to seek the patch-clamp hole, or other electrodes, may be used for the application of such a dielectrophoretic field while a test cell, preferably a single cell, is delivered into the nozzle. Once the cell reaches the region subject to the dielectrophoretic field produced by the electrodes, it becomes repelled and supported by the field; therefore, the motion of the cell is stopped. According to another aspect of the invention, another set of the electrodes positioned above the location where the cell becomes so suspended is used to create a second dielectrophoretic field. Thus, together these sets of electrodes create a retaining cage that suspends the cell directly above the patch aperture. If the field produced by the first set of electrodes, which is closest to the aperture, is turned off, the cell is no longer supported above the patch-clamp aperture while it continues to be repelled by the other electrode set. Thus, the cell is urged toward the bottom of the cell-delivery nozzle, bringing it in close proximity to the patch hole. Suction is then applied in a conventional manner across the pore and a high-resistance seal is established between the cell and the pore. The cell-delivery unit is then separated from the patch-clamp partition and moved over and aligned with another aperture using the procedure of the invention.

As a result of the approach followed by the invention, the cost of electrophysiological testing of biological membranes is greatly reduced because only the patch-clamp component is discarded after each set of tests, the cell-delivery component being a permanent and reusable part of the system. Moreover, because of the techniques used to align the cell dispenser to the patch apertures and to position the test cells in close proximity of the apertures, electrophysiological testing may be implemented automatically and economically at high throughputs.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

Figure 1:
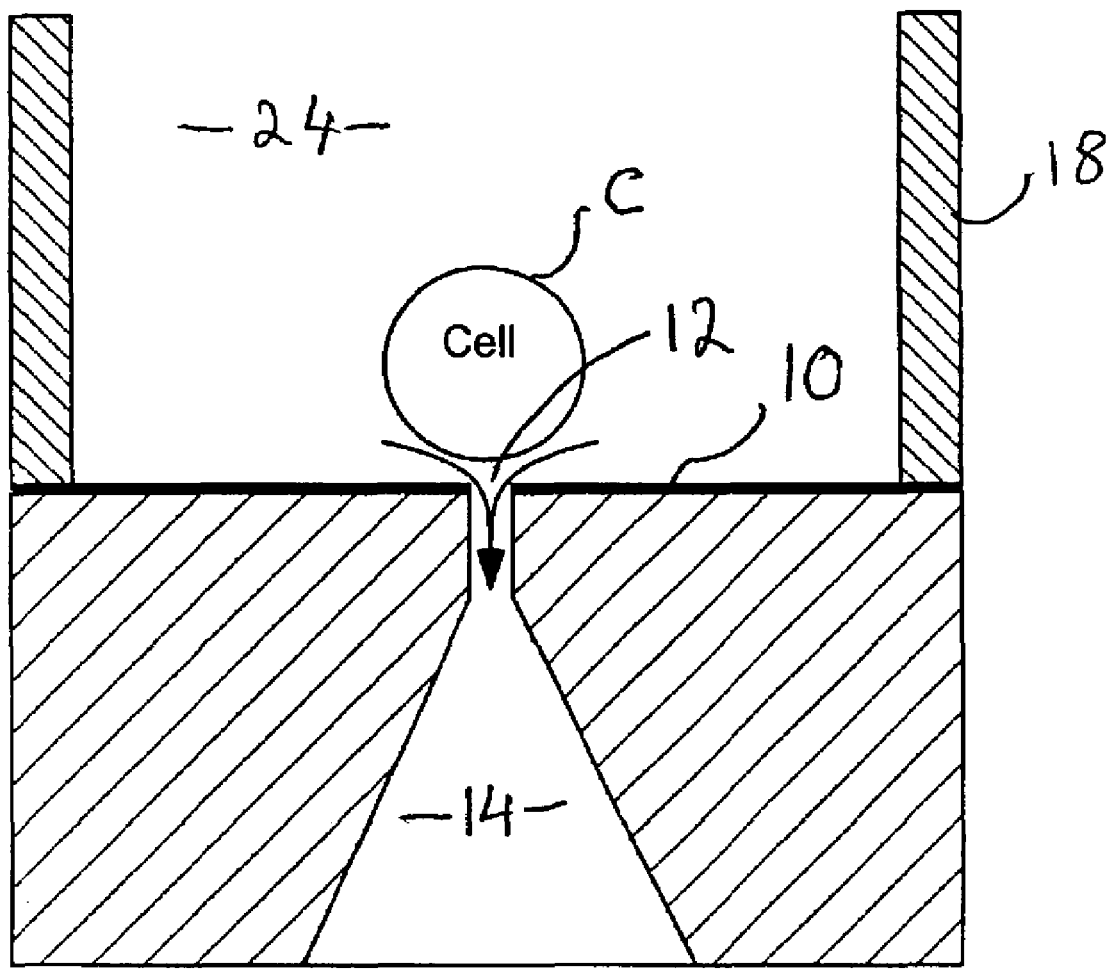
FIG. 1 is a schematic sectional representation of a perfusion chamber illustrating a test cell positioned in close proximity of a patch-clamp electrode aperture, so that passage of extracellular solution into the intracellular compartment is minimized when suction is applied to the intracellular compartment to bring the cell into the aperture and form a high-resistance seal.

An important aspect of this invention lies in the concept of using a cell-positioning device incorporated into a cell-delivery unit that is detachable from the patch-clamp component of a high-throughput electrophysiological testing assembly. Another aspect is the advantageous use of an electric field to perfect the alignment of the cell-delivery unit with each patch-clamp aperture. Yet another aspect is the use dielectrophoretic forces to precisely position a test cell over the patch-clamp aperture.

The term perfusion chamber is used herein to refer to a structure that includes an electrode-aperture partition separating an intracellular compartment from an extracellular compartment. The term extracellular solution is used to refer to the fluid in the extracellular compartment. Similarly, the term intracellular solution is used to refer to the fluid in the intracellular compartment.

The terms cell dispenser and cell-delivery unit are used interchangeably to refer to the movable and reusable part of the test assembly that is adapted for delivering test cells to the patch pores of the electrophysiological testing apparatus. The terms cell-positioning device and system are used interchangeably to refer to the apparatus adapted for positioning a test cell in the vicinity of a patch-clamp aperture. The cell-positioning device of the invention is contained within the cell dispenser. The terms patch-clamp partition, substrate and component are used interchangeably to refer to the disposable part of the test assembly that includes a partition separating each intracellular compartment from a corresponding extracellular compartment and an aperture, pore or hole therebetween suitable for forming a high-resistance patch-clamp seal. The terms aperture, pore and hole are also used interchangeably.

The term suction is used with reference to pressure applied at a given location to a body of fluid, tube, channel or compartment to refer to a condition wherein said pressure is less than the pressure applied at some other location to the body of fluid, tube, channel or compartment. The terms tube and channel refer to structures designed to direct fluid flow toward an exit orifice oriented in a particular direction. In particular, tube, channel and nozzle are also used in relation to that portion of the cell-delivery unit of the invention that is positioned over an aperture to deliver a test cell for patch clamping. Finally, the term dielectrophoretic cage is used to refer to any combination of electrodes adapted to produce dielectrophoretic fields capable of retaining a test cell within the volume defined by the spatial position of the electrodes.

The invention is described primarily with reference to cells, but it is understood that it applies to, and can be practiced in the same manner with, vesicles and other biological membranes. Therefore, the scope of the invention should not be limited to any particular test sample, so long as suitable for producing a patch-clamp seal as described herein.

Referring to the drawings, wherein the same reference numerals and symbols are used throughout for like parts, FIG. 1 is a schematic representation of the patch-clamp partition 10 of a perfusion chamber illustrating a test cell C positioned in close proximity of a patch-clamp electrode aperture 12. As the cell C approaches the edge of the aperture 12, the initial contact between the cell's membrane and the aperture is preferably established by suction from the intracellular compartment 14 in an underlying substrate 16. In order to minimize the passage of extracellular solution into the intracellular compartment when suction is applied, though, the cell first needs to be positioned in a zone within a few microns from the aperture by the cell-positioning system. Therefore, it is important that the cell-delivery unit be capable of directing the test cell toward the vicinity of the pore 12, as illustrated in the figure. A structure 18 schematically defining the extracellular compartment, which may include one or multiple patch holes, is shown for completeness of description.

Figure 2:
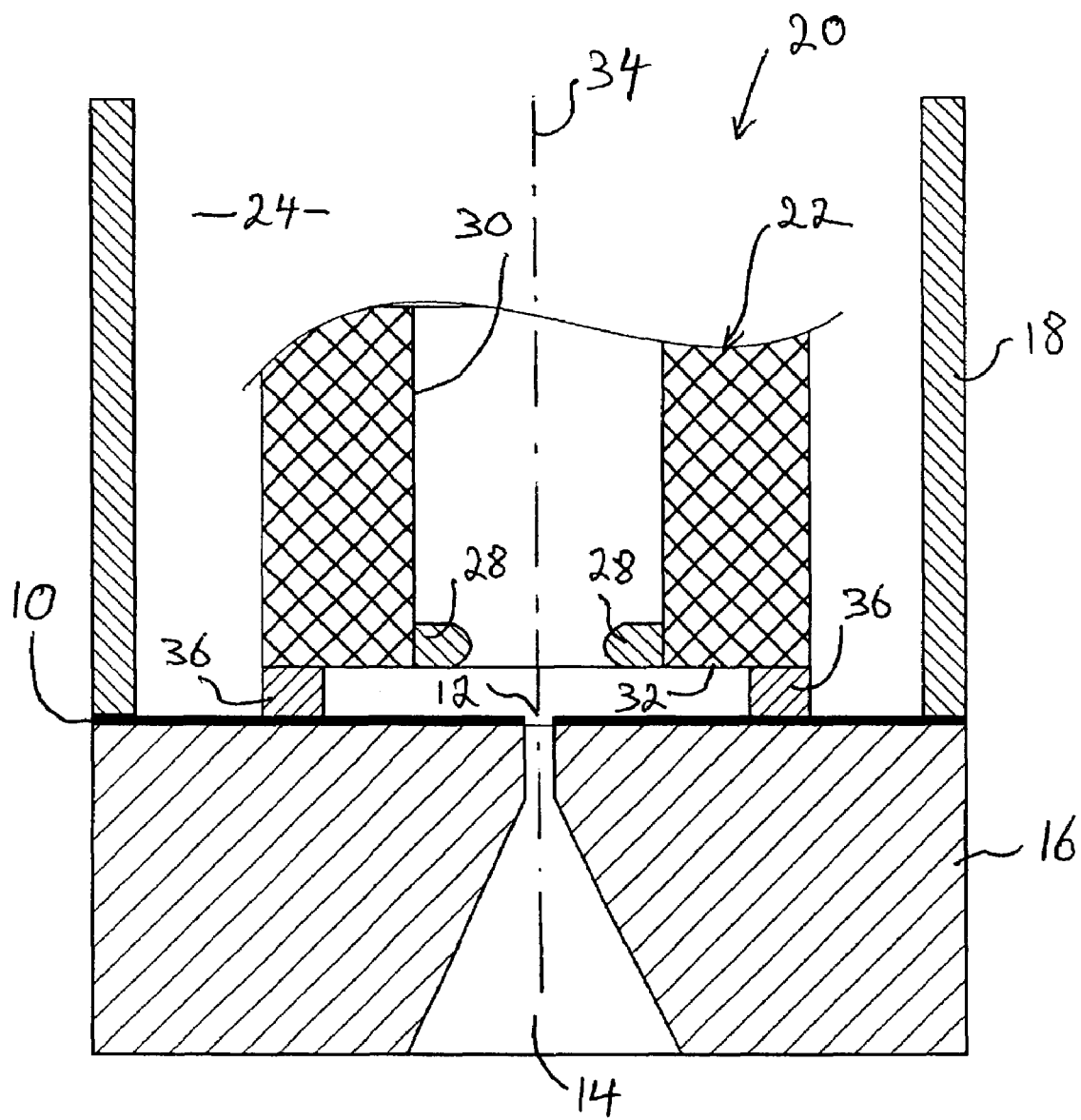
FIG. 2 is a partial section view of a cell-delivery unit positioned above a patch-clamp aperture according to the invention, wherein the vertical separation between the cell-delivery nozzle and the patch-clamp partition is determined by spacers and the horizontal alignment between the nozzle and the patch aperture is obtained by detecting an electric field emanating from the aperture with a set of electrodes inside the nozzle.
Figure 3:
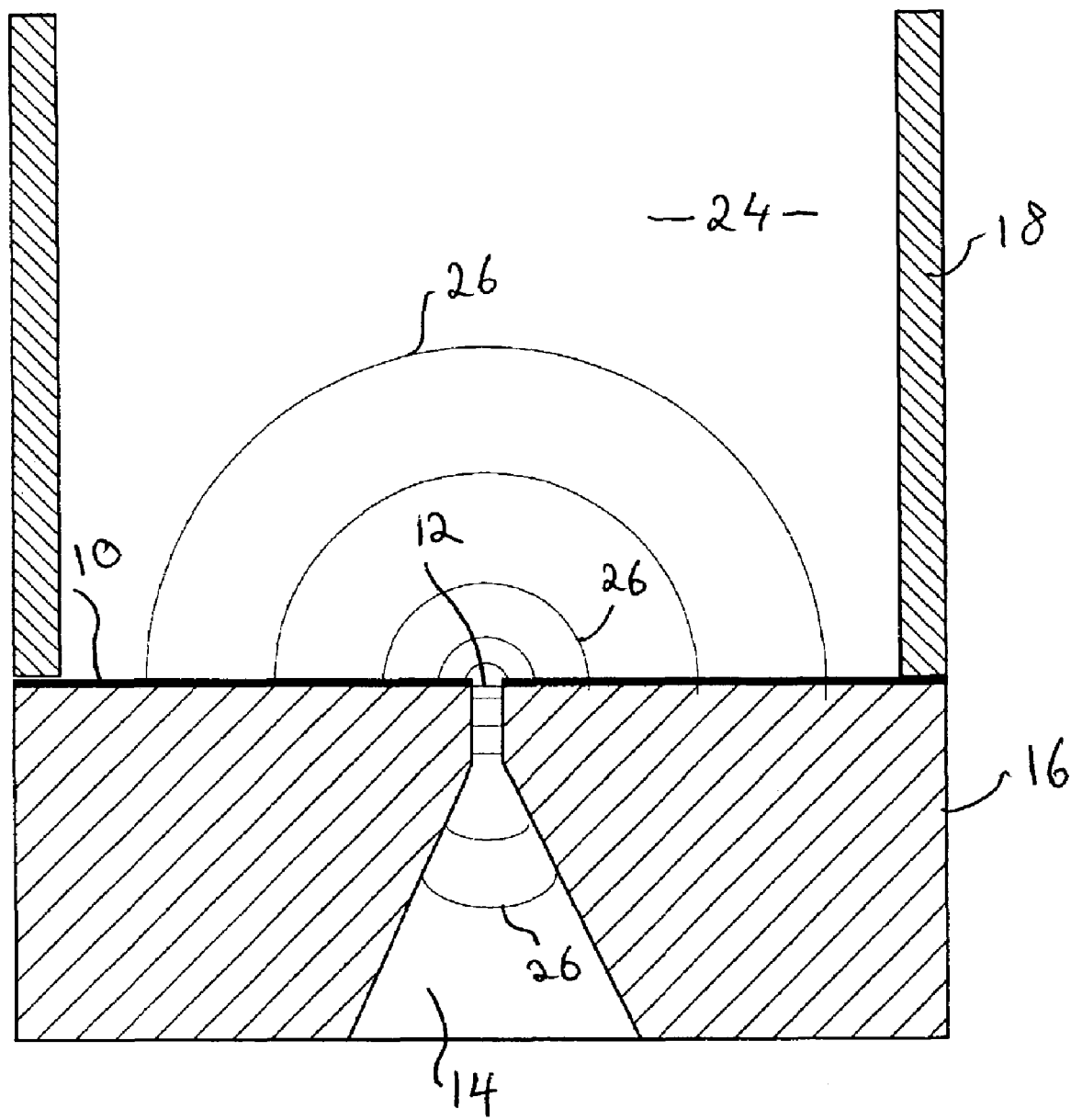
FIG. 3 is a diagram illustrating the equipotential lines of an electric field created by a voltage differential applied across the patch aperture.

In the prior art, the proximity of the initial placement of the cell C is limited by manufacturing tolerances for the coordinates of the aperture (typically +/−100–200 microns) and by the accuracy of the positioning mechanism. According to the invention, a movable cell-delivery unit 20 is utilized to sequentially operate on each patch-clamp hole 12 in a multi-aperture partition or substrate. The unit 14 includes a tubular bottom portion or nozzle 22 which is used to deliver a test cell over an aperture 12, as illustrated in FIG. 2. In order to optimize the positioning of a test cell C over the aperture 12, the axial alignment of the nozzle 22 with the center of the aperture is critical. Therefore, a voltage differential (either AC or DC, AC being preferable) is applied between the intracellular compartment 14 and the extracellular compartment 24 in which the nozzle 22 of the cell dispenser 20 is immersed. Appropriate electrodes (not shown) used to apply this voltage potential may be incorporated into the structures of the substrate 16 and tube 22. As a result of this condition, an electric field permeating both the extracellular and intracellular compartments is created, as illustrated in FIG. 3. As one skilled in the art would readily recognize, equipotential surfaces 26 of the electric field (shown as lines in the two-dimensional representation of the drawings) are formed above and below the aperture 12, the field being strongest next to the aperture. In particular, the circular geometry of the aperture 12 produces very regular equipotential surfaces in the extracellular compartment 24 of the cell-delivery nozzle 22.

Figure 4:
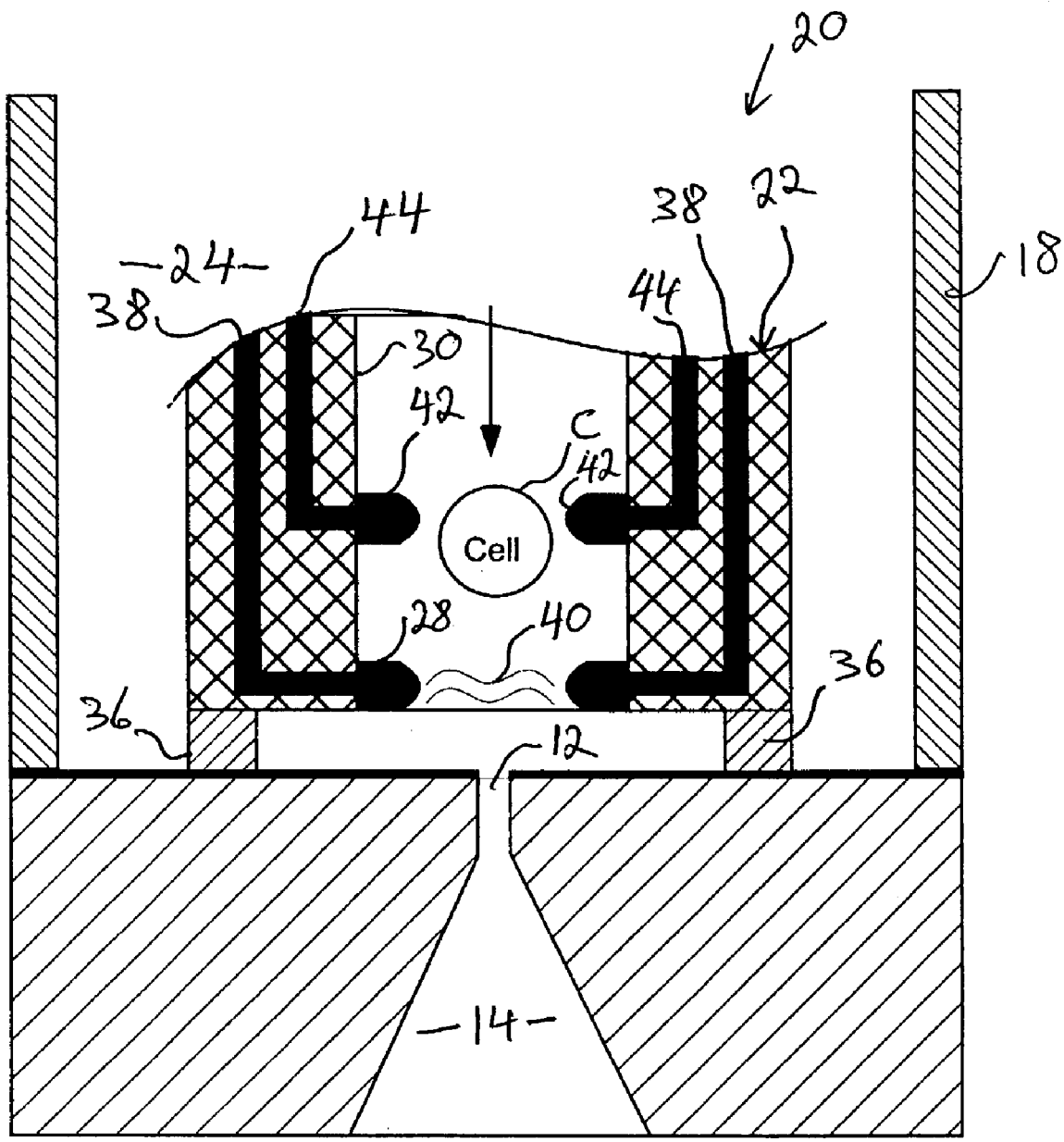
FIG. 4 illustrates a test cell being delivered through a dispensing nozzle wherein a lower dielectrophoretic field is used to suspend the cell close to the end of the nozzle.

According to one aspect of the invention, electrodes 28 (multiple electrodes are preferred) are placed on the nozzle 22, preferably along the bottom of the interior wall 30 thereof. Inasmuch as in the preferred embodiment of the invention the cell delivery system is essentially a tube (round or other shape, such as rectangular, in cross-section), the electrodes 28 may consist simply of a conductive film deposited on the surface inside or outside the tube, preferably close to the tip. Regardless of the specific geometry of the lower tubular portion of the nozzle 22, any number of electrodes 28 may be used to detect the electric field in the extracellular compartment. Preferably, at least two (optimally four) electrodes 28 are used, uniformly placed around the tube 22 at equal distance from its main axis 34 and on a plane substantially normal to the axis. Nonetheless, those skilled in the art will recognize that these conditions are not critical to the invention because any number of electrodes positioned in any known manner in the nozzle 22 may be used to detect the electric field and calculate the location of the nozzle on the basis of its strength. The electrodes are connected to amplifiers by conductors 38 that are preferably embedded in the cell-dispenser body (as shown in FIG. 4).

When the nozzle 22 of the cell dispenser 20 is brought into proximity of the partition 10, as illustrated in FIG. 2, each electrode 28 measures a potential (with respect to some reference) in the extracellular solution produced by the voltage differential applied between the intracellular and the extracellular compartments. Since the electric field in the extracellular compartment emanates from the patch aperture 12, if the electrodes 28 are uniformly distributed with respect to the nozzle's axis, it is clear that the potential measured at all the electrodes is equal when the nozzle is centered over the aperture. Accordingly, this feature is advantageously utilized to guide the alignment of the cell dispenser 20 with each patch-clamp aperture 12 during the sequential delivery of test cells in a multi-well patch-clamp tray. Utilizing an external, computer-controlled, XYZ actuator with feedback from the electrodes 28, the cell-delivery system is moved around the aperture 12 until the potentials measured by all electrodes are equal. Thus, an active "hole-seeking" device and procedure are used to align the nozzle of the movable cell-delivery unit with the patch aperture 12. Conventional techniques may be used to implement this procedure. For example, a computer may record the potential measured by all electrodes and position the nozzle so that the sum of such potentials is maximized (indicating a close proximity to the patch aperture) and the difference in the potential measured at each electrode is minimized (indicating alignment with the aperture's centerline).

Thus, the horizontal alignment of the nozzle 22 of the cell-delivery unit with each patch-clamp hole 12 is performed by actively seeking the hole while monitoring the potential measured with the electrodes 28 inside the delivery channel in the nozzle. The vertical position of the cell dispenser may be set using small spacers 36 attached to the bottom 32 or to the sides of the nozzle 22. The spacers 36 preferably extend beyond the bottom part of the cell dispenser, as illustrated in FIG. 2, far enough away from its axis 34 to minimize interference with the patch aperture 12 during the dispenser-positioning procedure. If spacers are used, the nozzle 22 of the dispenser, which is preferably spring-loaded, is brought to the patch-clamp substrate 10 until the spacers 36 touch the substrate, thus registering the dispenser vertically. Therefore, is such case the vertical positioning of the system relies on mechanical contact between the spacers 36 and the substrate 10.

Once the movable nozzle 22 has been properly centered around a patch hole 12, a test cell C is delivered for patch clamping to the hole 12. To this end, the cell C needs to be positioned as close as possible to the aperture before suction is applied in the intracellular compartment 14, as explained above. According to another aspect of the invention, the positioning of the test cell is accomplished by applying an electric voltage suitable to create a dielectrophoretic field (typically, an AC voltage in the order of about 10 volts with a frequency range of 100 Hz to 100 MHz) between electrodes placed at the bottom of the tube 22. The same electrodes 28 used to seek the hole 12 (illustrated in FIG. 4), or a different set of at least two electrodes, may be utilized for producing the dielectrophoretic field. The electrodes are connected to outputs of generators via electrical switches. The generators produce electrical voltages suitable for producing dielectrophoretic fields. A test cell C, preferably a single cell, is delivered through the channel in the nozzle 22 from the top of the cell dispenser 20. The cell may be delivered by a flow of solution, by gravity, by dielectrophoresis, or by any other means known in the art. The cell is preferably preliminarily sorted and cleaned of debris by a conventional cell sorter or a cell sorter based on dielectrophoresis. Once the cell is placed in the nozzle 22 of the dispenser and reaches the region over the dielectrophoretic field 40 created by the electrodes 28, the motion of the cell C is interrupted and the cell becomes supported by the dielectrophoretic field.

Figure 5:
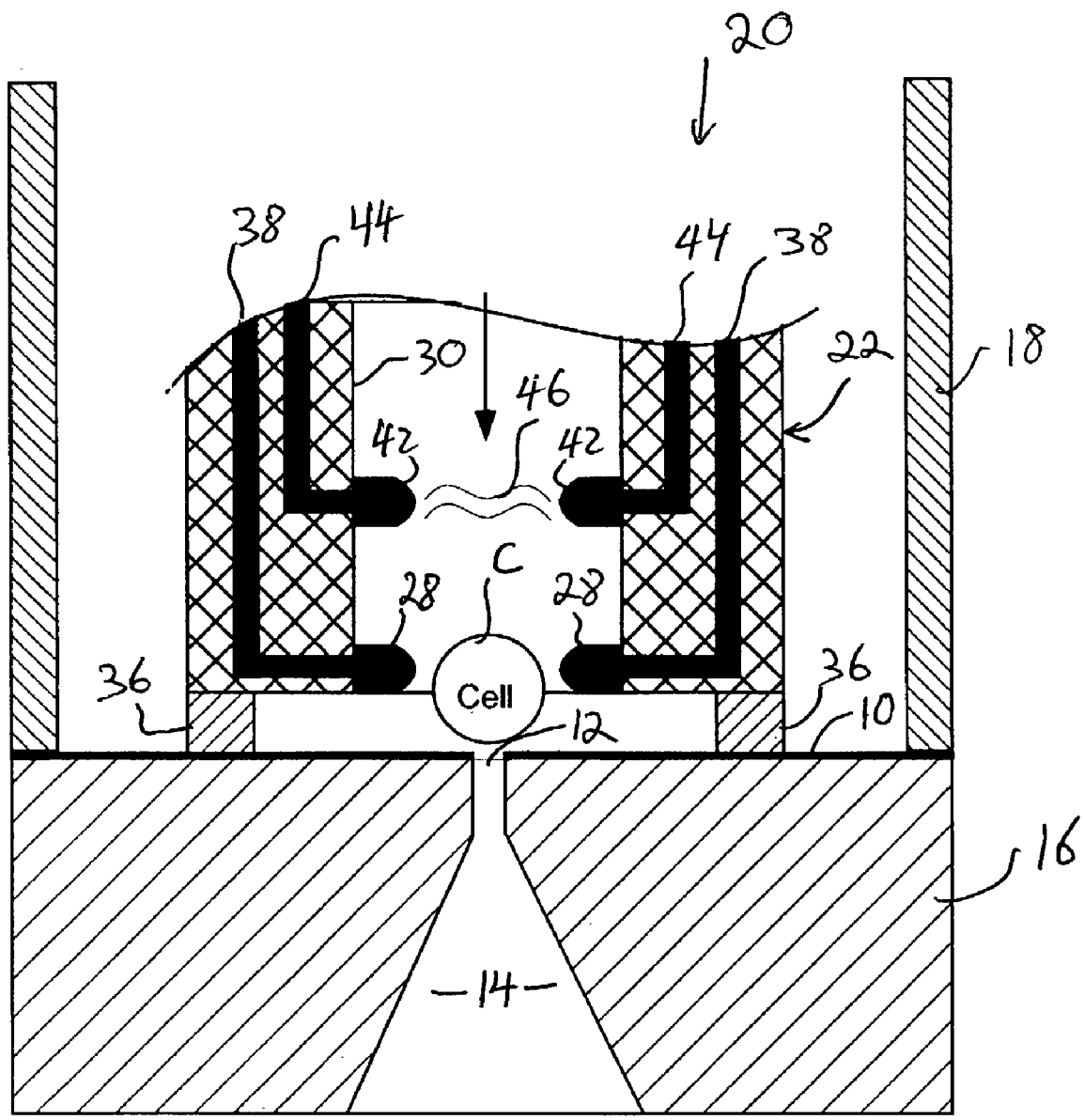
FIG. 5 illustrates the test cell of FIG. 4 being urged toward the patch pore by an upper dielectrophoretic field after termination of the lower field.

Another set of electrodes 42 (at least two, but preferably 4) is positioned above the location where the cell is suspended. The electrodes 42 may also consist of a conductive metal film deposited on the interior wall 30 of the nozzle 22 and are connected to amplifiers by conductors 44 that are preferably embedded in the cell dispenser, as shown in FIG. 4. Together with the first set of electrodes 28 (which are lower, or distal, with reference to the cell-delivery unit), the upper or proximal electrodes 42 create a cage (an octopole, if each set includes four electrodes) for the cell C. When a dielectrophoretic field is also applied between the electrodes 42, the cell C becomes trapped in the cage and suspended directly above the patch aperture 12. If the dielectrophoretic field 40 produced by the bottom set of electrodes 28 is turned off, the cell C is no longer supported, but becomes instead subject only to the repelling forces of the dielectrophoretic field 46 produced by the top electrodes 42, as shown in FIG. 5. Accordingly, the cell C is urged toward the patch hole 12. As suction is applied across the pore, the seal of the cell C to the pore is established for patch-clamp testing. The XYZ positioner lifts the nozzle 22 of the cell dispenser and translates it over another well, where the nozzle is aligned again with the next patch hole 12 and another cell is positioned onto the pore according to the invention. The procedure is automated and repeated sequentially for rapid testing carried out over multi-well patch-clamp trays.

Figure 6:
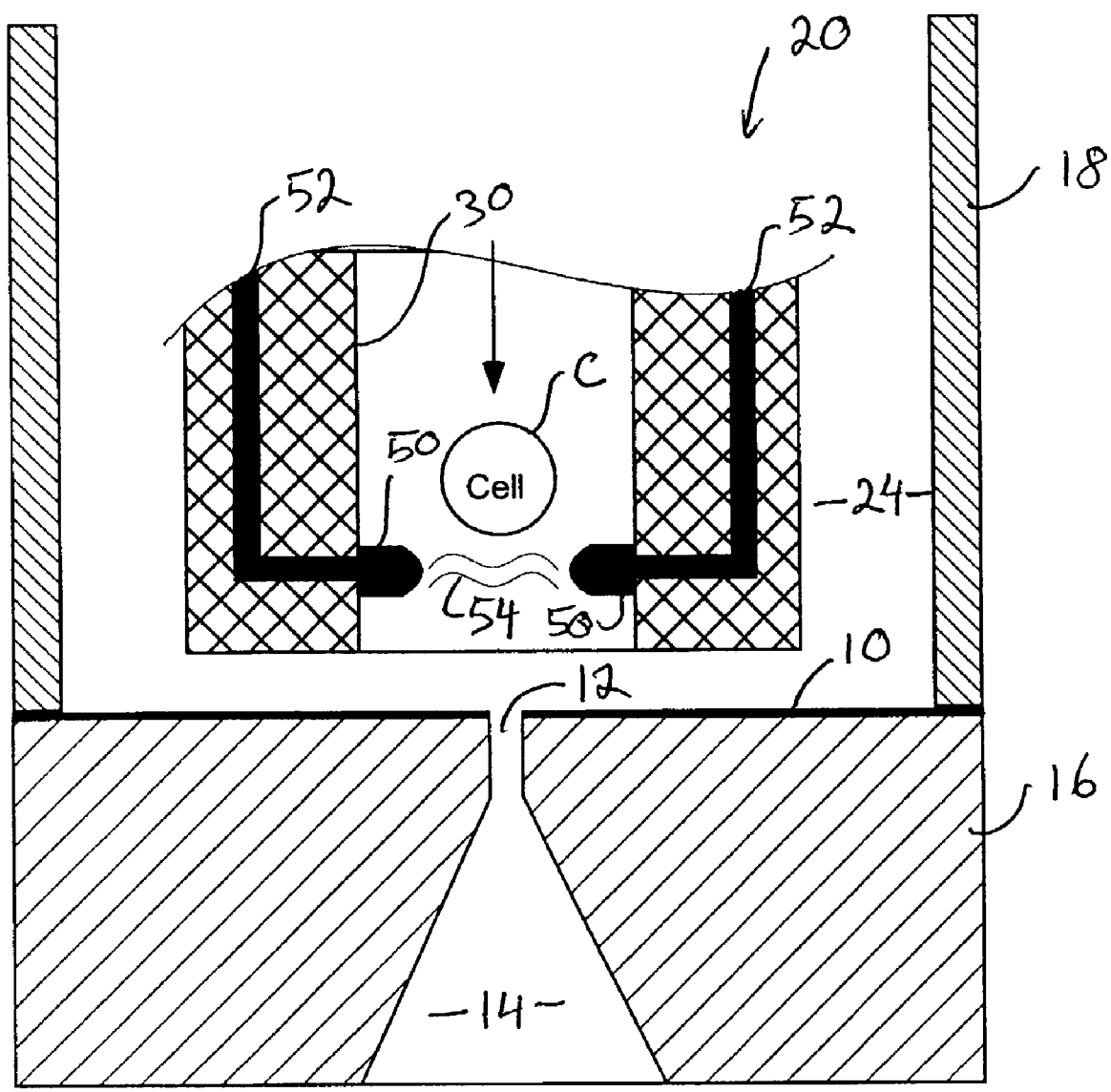
FIG. 6 illustrates another embodiment of the dielectrophoretic-field cell-positioning system of the invention wherein a single set of electrodes is employed.

As described, if each set of electrodes 28,42 includes four units, the resulting eight electrodes on the wall 30 (or walls, in case of a multi-faceted channel) of the nozzle 22 create an octopole cage to position the cells. In order to simplify the delivery system, a simple quadrupole-electrode arrangement 50 (similarly connected to amplifiers by conductors 52 preferably embedded in the cell dispenser) may be utilized at the end of the cell-delivery nozzle, as shown in FIG. 6 in an embodiment without spacers 36. In this configuration, the test cell C is first suspended in extracellular solution above the quadrupole 50 and the patch aperture 12 by a dielectrophoretic field 54 created by the quadrupole. The field is then briefly switched off, allowing the cell C to be carried toward the hole 12 by the solution flow. After the cell passes the electrodes 50, the dielectrophoretic field is turned on again, re-establishing a field that pushes the cell toward the patch aperture (such field being strongest along the axis of alignment to the aperture).

Figure 7:
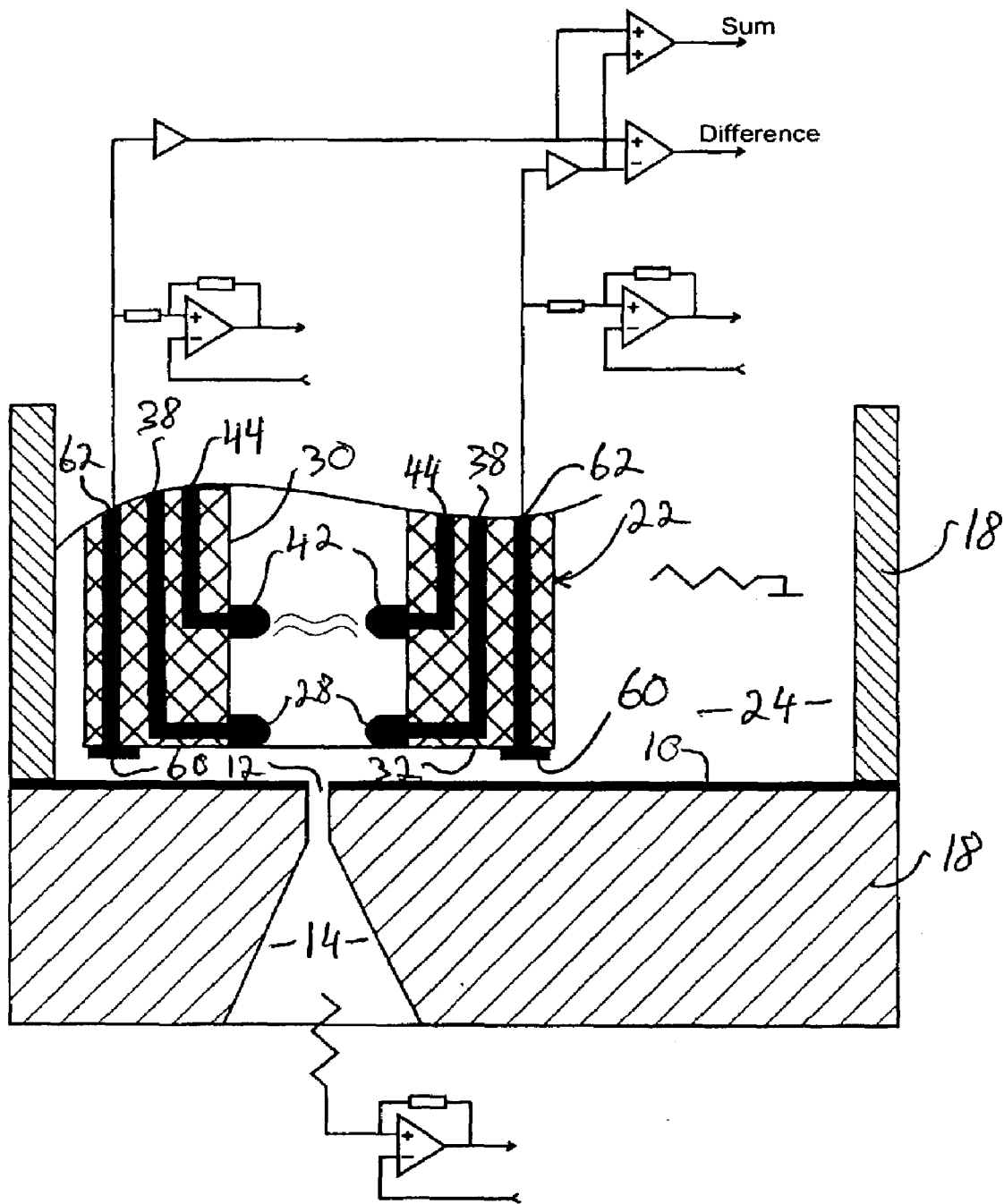
FIG. 7 shows a cell-delivery nozzle according to the invention with separate sensing electrodes placed at the bottom of the unit.

Since the tip of the nozzle of the delivery system 20 is rather small (in the order of a fraction of a millimeter across), the spacers 36 are necessarily also very small. Therefore, the pressure exerted by the spacers onto the substrate 10 tends to be large even if the force exerted as a result of mechanical contact is not large. This pressure may damage the substrate and/or the tip of the nozzle. Therefore, it is very undesirable. Accordingly, in yet another embodiment of the invention illustrated in FIG. 7, sensing electrodes 60, which may be different from the dielectrophoretic-field producing electrodes discussed above, are deposited face-down on the bottom 32 of the cell-delivery nozzle. The electrodes 60 are preferably made by photolithography or metal sputtering on a glass substrate, with subsequent bonding to the substrate (such as by anodic bonding). As shown in FIG. 7, the electrodes 60 are connected to high-impedance amplifiers and to resistance measuring circuits in conventional manner by conductors 62 preferably embedded in the nozzle of the delivery unit. After transferring the nozzle to a well and after crude initial positioning of the system is achieved with respect to the patch pore in the well pore within the mechanical tolerances of the translation mechanism, the nozzle 22 is slowly moved down until the sensing electrodes 60 come in close proximity of the surface of the substrate 10. This can be detected by measuring resistance at the electrodes 60, which increases as the electrodes become closer to and possibly touch the substrate 10, which is electrically insulating. Therefore, this operation can be monitored and carried out automatically. When close proximity of the nozzle with the substrate is sensed, the dispenser is preferably lifted enough to provide a small gap and allow the continued flow of extracellular solution. Then, the X-Y registration of the nozzle 22 with respect to the patch pore 12 is performed as detailed above (that is, position-detection pulses are applied through the pore and measured by the electrodes 60 until the unit is perfectly centered around the patch aperture). It is noted that while the vertical registration has been described above as being performed prior to the horizontal registration, it is possible to do so effectively only when the patch-clamp partition is perfectly flat. Therefore, it is generally preferable to first carry out the horizontal registration and then follow with the vertical registration.

Thus, a movable cell-delivery system has been described that is advantageously suitable for high-throughout applications. The positioning shortcomings imposed by tolerances of mechanical actuators are overcome for automated operation by the combination of electrode sets provided by the invention, which enable the rapid and precise placement of both the dispensing unit and the test cell with respect to each patch hole on a multi-well patch-clamp partition. Obviously, testing can be further accelerated by utilizing multiple dispensers working in parallel to sequentially deliver test cells to patch holes in a multi-well tray.

Figure 8:
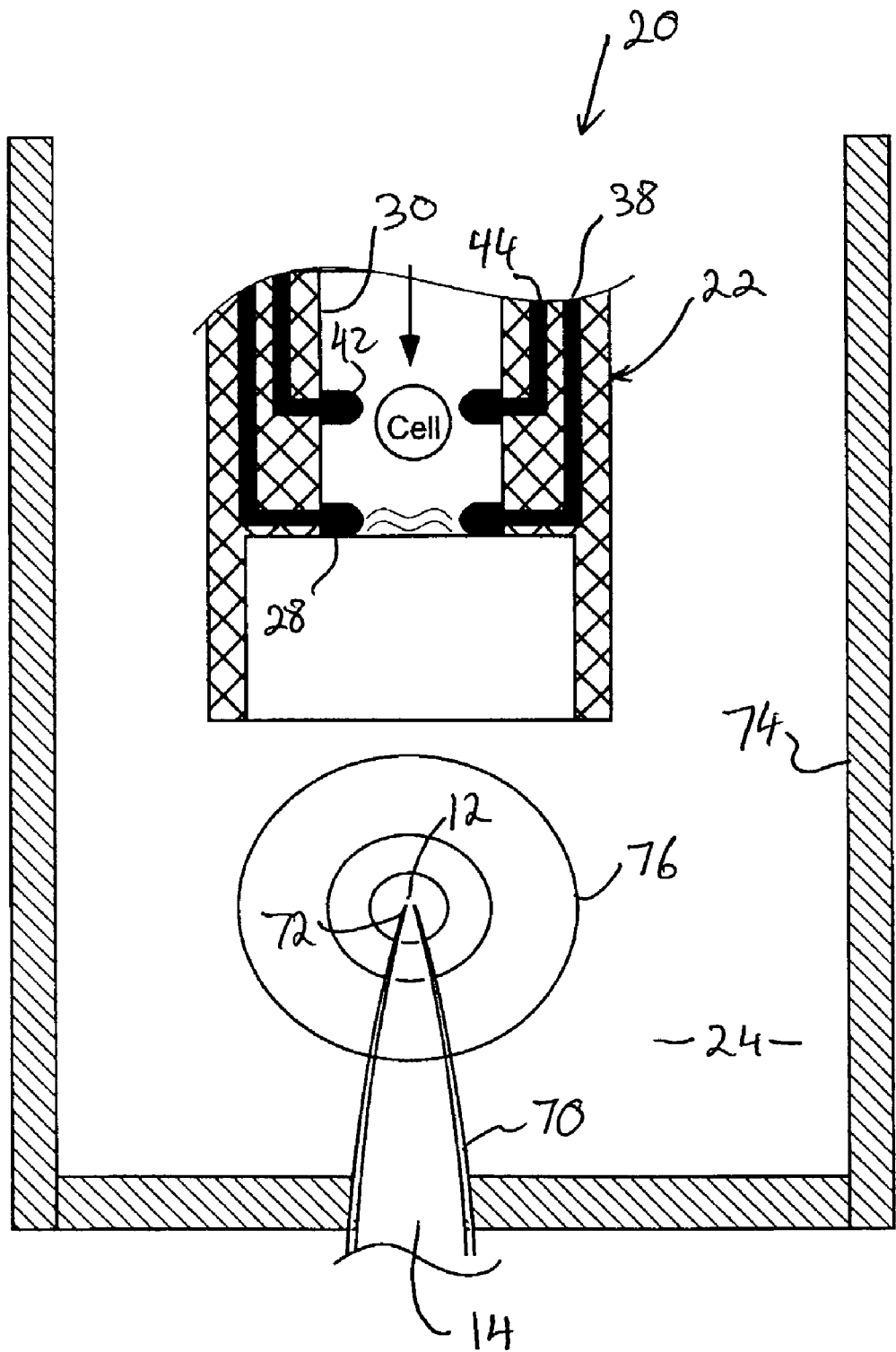
FIG. 8 illustrates another embodiment wherein the cell-delivery unit of the invention is used with a conventional patch-clamp pipette.
Figure 9:
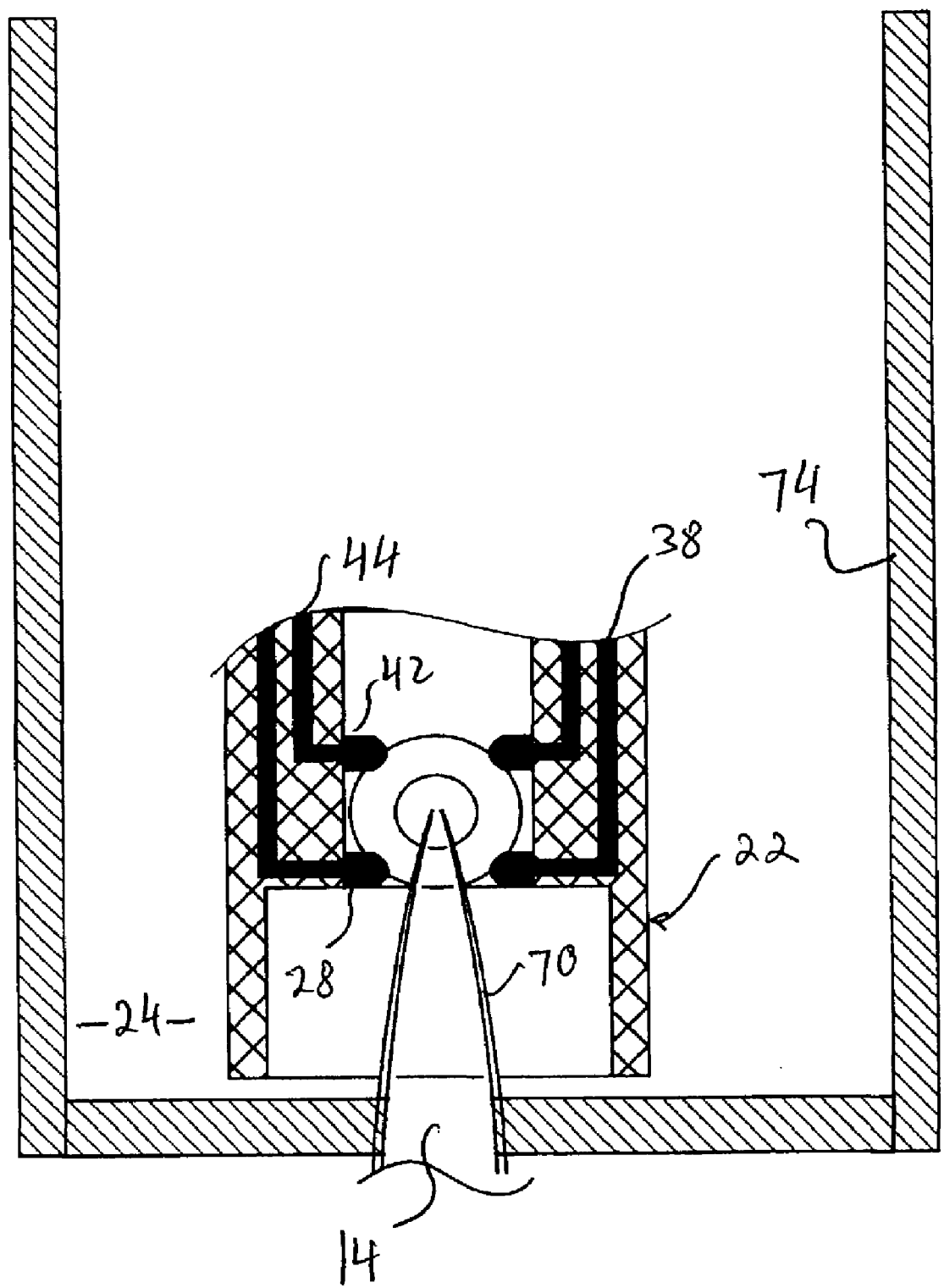
FIG. 9 shows the system of FIG. 8 where the pipette has been placed within the dielectrophoretic cage defined by the sets of electrodes in the delivery channel of the cell dispenser.

The invention has been described with reference to patch-clamp that utilize planar or similar patch-hole partitions, but it can be used as well to deliver a test cell to a single-aperture test apparatus or to the patch pore of a conventional patch pipette. For this application, the nozzle of the cell-delivery system needs to be positioned in the X, Y and Z dimensions around the pore in the tip of the pipette. As illustrated in FIG. 8, the patch pipette 70 can be positioned vertically, with the tip 72 facing up, close to bottom of a recording chamber 74. The nozzle 22 of the cell-delivery unit is brought into the chamber 74 by the XYZ positioning system, so that it is roughly positioned directly above the pipette, as seen in the figure. A test voltage (preferably AC) is applied through the pore 12 in the tip of the pipette to create an electric field with equipotential surfaces (lines 76 in the figure) that can be detected by the electrodes 28 inside the nozzle 22 of the cell-delivery unit, as described above. As in the case dealing with a patch-clamp pore, the control computer moves the nozzle 22 (and the recording chamber 74, which includes an extracellular compartment 24) in X-Y until the signal received by the electrodes indicates that the cell-delivery unit is precisely placed over the tip of the pipette. The nozzle 22 is then lowered slowly, further controlling its X-Y position to maintain the axial alignment with the tip of the pipette using the signal sensed by the electrodes 28 (as discussed above). Proceeding in this manner, the tip 72 of the pipette is inserted into the channel of the nozzle 22 where the sets of electrodes 28 and 42 are utilized to create the dielectrophoretic cage used to position the test cell. As discussed above, these electrodes are connected to corresponding sets of high-impedance amplifiers to measure the voltage picked up by each electrode. Thus, these electrodes are advantageously used to control the motion of the nozzle 22 so that the tip of the pipette 72 in placed in the center of the cage, as illustrated in FIG. 9.

At this point, the cell-positioning procedure discussed above with reference to FIGS. 5 and 6 is initiated. A test cell is delivered into the nozzle unit 22 and placed within the cage by the sequential use of the sets of electrodes 28 and 42. Once the cell is suspended in the cage, the cell dispenser is lowered until the pipette's tip touches the cell, which can be detected by the increased resistance measured across the pore using conventional patch-clamp hardware. Suction is then applied to form a giga-seal between the pipette and the cell, as in standard patch-clamp testing with pipettes. The process is then repeated after conclusion of the test by transporting the cell-delivery system to another recording chamber (or well in a multi-well plate) associated with another pipette tip.

Figure 10:
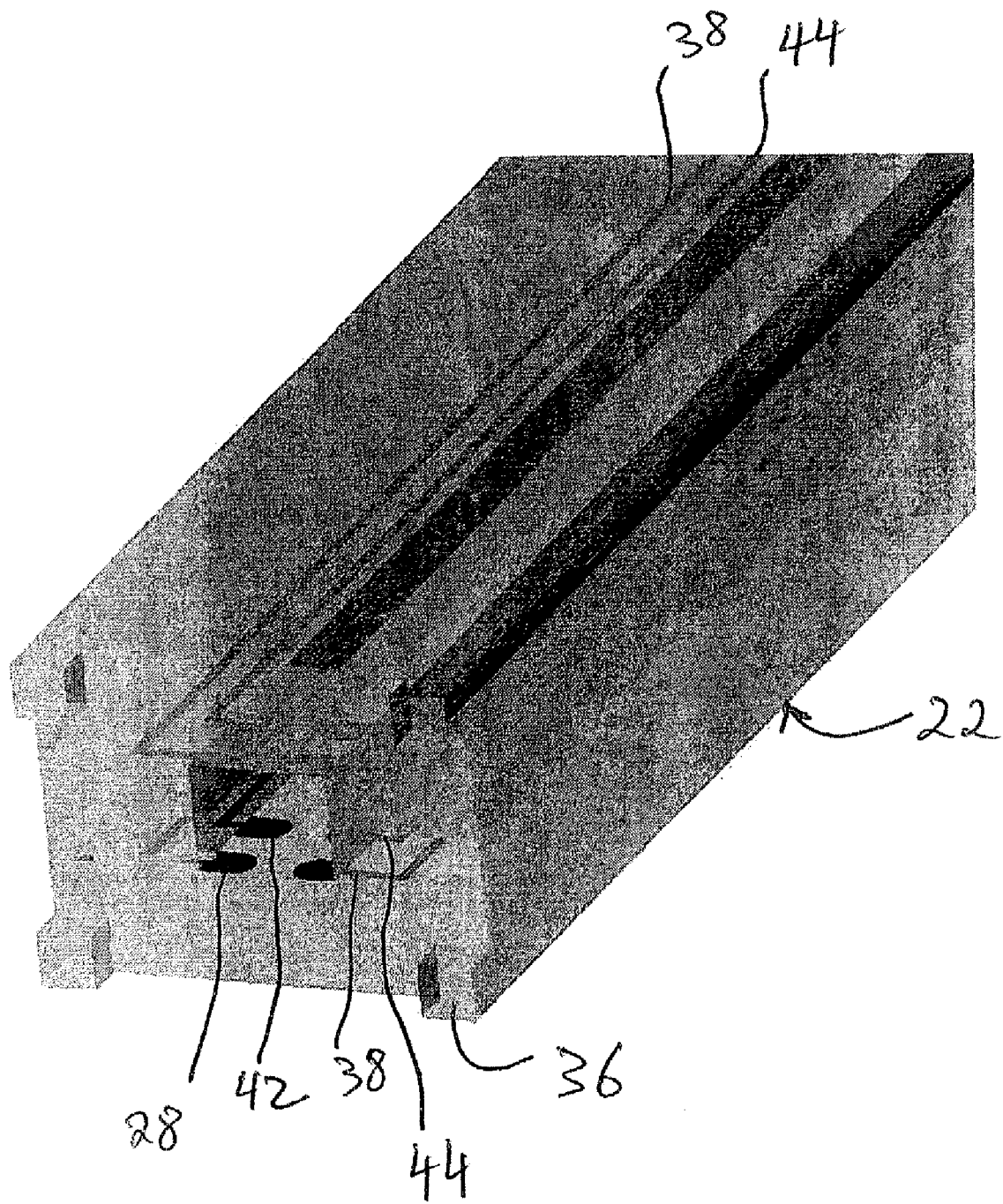
FIG. 10 is a three-dimensional representation of the cell-delivery unit of FIG. 5, showing a nozzle with a rectangular channel for cell transfer and eight electrodes deposited on its walls to create an octopole dielectrophoretic cage.
Figure 11:
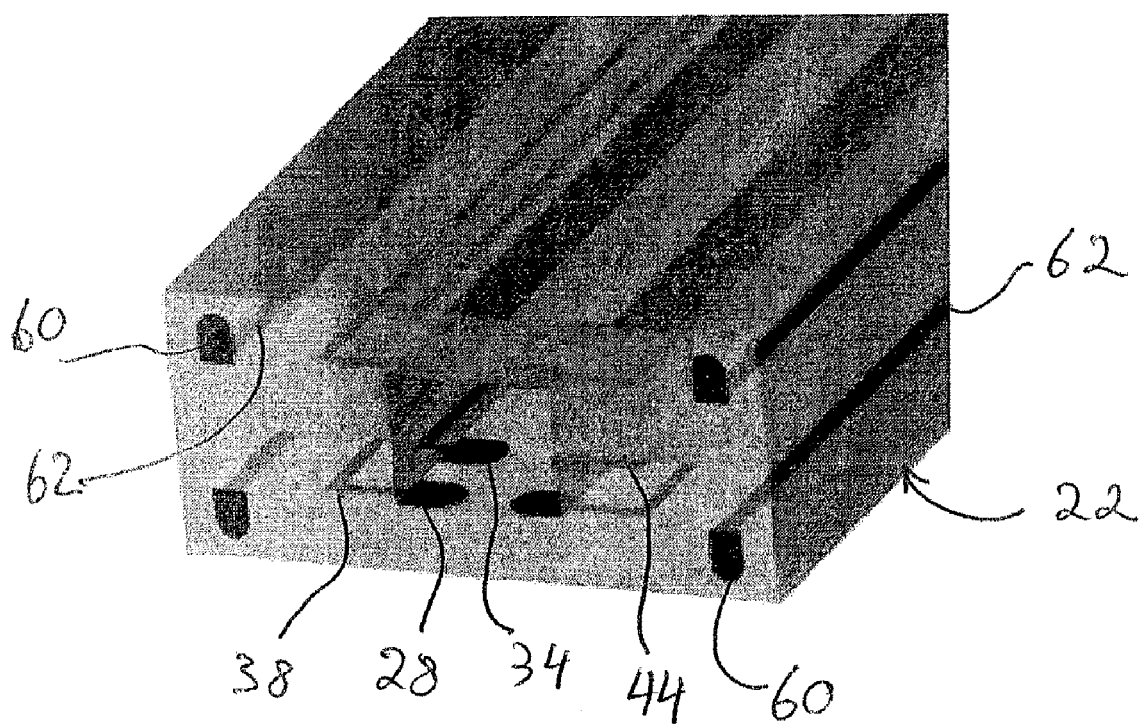
FIG. 11 is a three-dimensional representation of the cell-delivery unit of FIG. 7, showing a nozzle with a rectangular channel, eight dielectrophoretic electrodes, and four additional sensing electrodes deposited on the bottom of the nozzle.

Thus, several approaches have been described to produce movable cell dispensers suitable for sequential delivery of test cells to test trays with arrays of electrode apertures to practice automated sequential testing of a plurality of test cells. As is well understood in the art, in order to accomplish the goals of the invention, each electrode aperture must be incorporated into a structure containing an intracellular compartment electrically connected to an electrode through an intracellular solution. The cell-delivery unit of the invention must also provide a compartment where the test cells are suspended in extracellular solution for delivery to the electrode aperture, and the entire assembly must be connected to a fluidic system with appropriate valving and pressure/vacuum sources to feed and withdraw the extracellular and intracellular solutions through appropriate channels, as done for conventional electrophysiological recording. FIGS. 10 and 11 illustrate in three dimensions actual implementations of the cell-delivery units of FIG. 5 and FIG. 7, respectively, wherein a nozzle with a rectangular channel is used for cell transfer and eight electrodes deposited on its walls are used to create an octopole dielectrophoretic cage.

Figure 12:
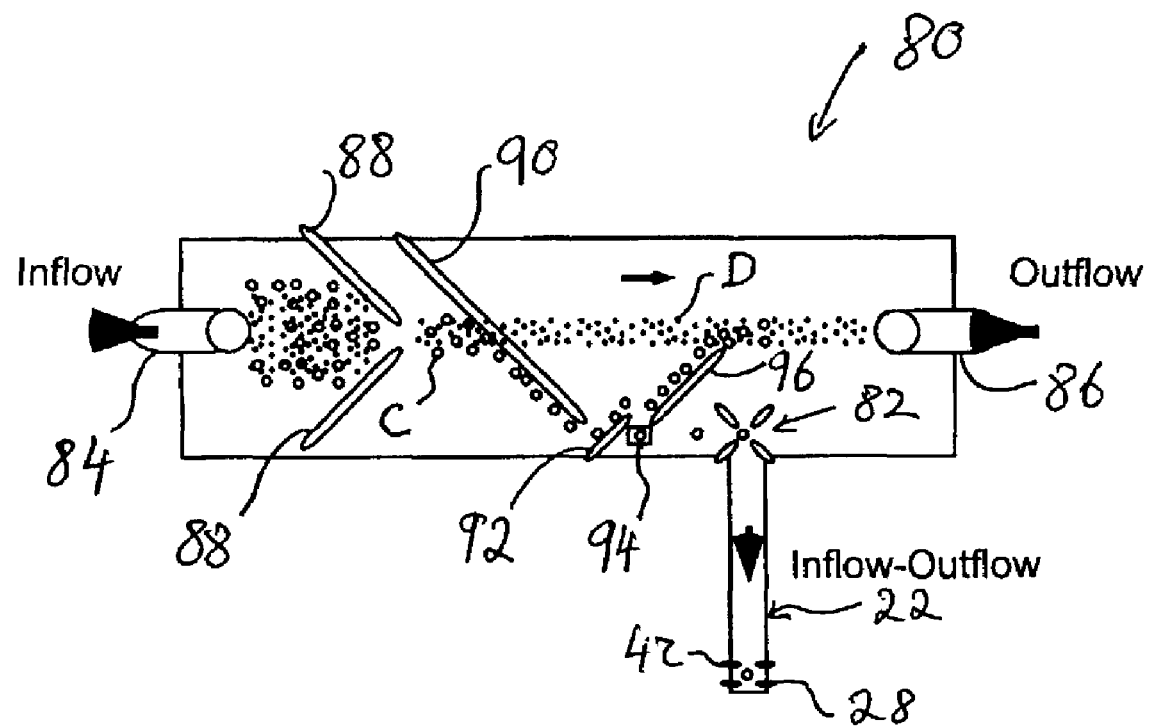
FIG. 12 illustrates a cell sorter integrated with the cell-delivery system of the invention.

A cell sorter may be combined with the cell-delivery system of the invention in order to separate test cells from debris and facilitate the delivery of a single cell to the cell delivery nozzle. The same concept utilized to position a test cell over a patch hole or a pipette tip can be used advantageously also to sort cells and deliver a single cell to the dispenser of the invention. As illustrated in FIG. 12, a cell-sorter unit 80 may include a multipole (preferably octopole) dielectrophoretic cage 82 at the top of the dispenser tube 22, the cage 82 being similar to the cage produced by the sets of electrodes 28,42 in the bottom portion of the tube. The sorter would include an inlet port 84 connected to a syringe pump (not shown) injecting a stream of extracellular solution with suspended cells C into the sorter, and a waste port 86 connected to another syringe pump (not shown). A flow-focusing structure consisting of four electrode plates 88 of metal-coated glass or other electrically insulating material may be provided to direct the flow toward a cavity feeding a sorter 90 consisting of a pair of parallel dielectrophoretic electrodes. Through the effect of separate dielectrophoretic fields, the electrodes 88 produce a concentration of test cells directed toward the sorter 90, and the sorter in turn allows passage of debris D while blocking passage of the cells. An electronic gate 92 and a cell detector 94 (such as a multi-frequency particle impedance detector) are provided at the bottom of the sorter 90 to direct the cells C either to waste or to the octopole cage 82.

In operation, the cell suspension is pumped into the inlet port 84 at a certain flow rate. The outflow pump is operated to suck the waste solution from the outflow port 86 at a lower rate, the difference between these rates being the desired flow rate of solution to the cell delivery nozzle 22. The cell suspension from the inlet port is sorted to separate the cells from the debris particles (which are repelled less than the cells by the dielectrophoretic forces of the sorting electrodes), which go directly to the waste port 86. The sorted cells at the bottom of the sorter 90 pass over the electronic gate 92 which, when energized, places the cells over a baffle 96 that directs them to the waste outflow port. When the gate 92 is de-energized, the cells are allowed to pass on toward the cell detector 94 which, upon detection of a cell, provides a signal to start the sequence of steps necessary to energize the electrodes of the dielectrophoretic cage 82 in order to catch and suspend the cell at the mouth of the cell-delivery unit. The nozzle 22 of the cell-delivery unit is then positioned above the patch pore in a planar substrate (or above the pore in a patch pipette system), as described above. When the initial positioning of the nozzle 22 is completed, the bottom half of the octopole 82 is de-energized, so that the top set of electrodes repels the cell into the delivery channel, where it is caught by the lower octopole sets of electrodes 28,42 and then is delivered to the patch pore as explained above. The sorter and cell-delivery unit are then transported to a new well and the process is repeated.

Figure 13:
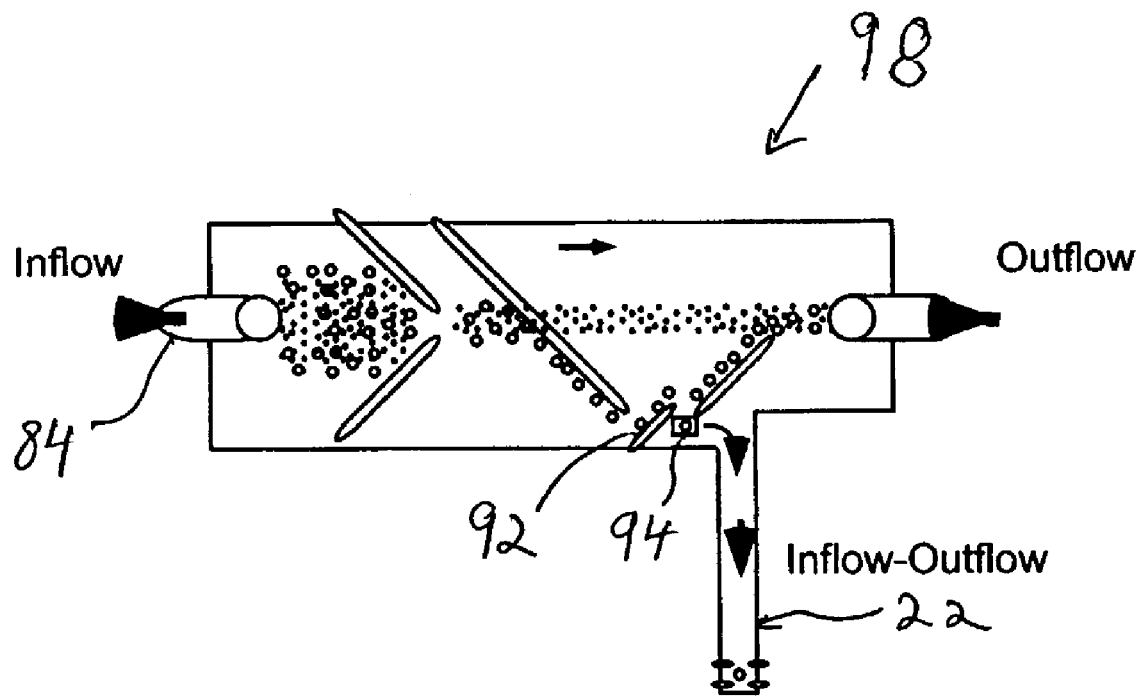
FIG. 13 illustrates a simplified cell sorter, wherein a single cell is separated and driven into the cell delivery nozzle by laminar flow of extracellular solution.

Various changes in the details, steps and components that have been described may be made by those skilled in the art within the principles and scope of the invention herein illustrated and defined in the appended claims. Thus, it is understood that the concept of the invention may be implemented in equivalent fashion with different structural configurations than detailed herein. For example, any combination of sets of electrodes, each set containing at least two electrodes (preferably three or four) preferably uniformly disposed around the axis of the delivery channel, may be used to provide the cage effect used in the preferred embodiment of the invention. Similarly, the cell sorter 80 of FIG. 12 could be simplified by eliminating the dielectrophoretic cage 82 and relying instead solely on the action of the electronic gate 92 and the cell detector 94 to release each test cell to the delivery tube 22. Such an embodiment 98 is illustrated in FIG. 13.

Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and procedures.

We claim:

1. A cell-delivery unit for delivering a test cell to a patch-clamp electrode structure, comprising:
    a fluidic channel adapted to deliver a biological membrane toward a nozzle facing said patch-clamp electrode structure;
    at least one sensing electrode disposed at a predetermined position with respect said nozzle;
    means for detecting signals corresponding to an electric field emanating from said patch-clamp electrode structure with said at least one sensing electrode; and
    means for positioning the nozzle so as to align an axis thereof with the patch-clamp electrode structure using said signals detected by the at least one sensing electrode.

2. The cell-delivery unit of claim 1, comprising at least two sensing electrodes and further including means for producing a first dielectrophoretic field using said sensing electrodes.

3. The cell-delivery unit of claim 2, further including:
    at least two positioning electrodes in the nozzle; and
    means for producing a second dielectrophoretic field using said positioning electrodes.

4. The cell-delivery unit of claim 3, wherein said patch-clamp electrode is a patch-clamp aperture in a partition.

5. The cell-delivery unit of claim 3, wherein said patch-clamp electrode is a patch-clamp pore in a pipette.

6. The cell-delivery unit of claim 3, wherein said at least one sensing electrode disposed at a predetermined position on said nozzle comprises at least two electrodes positioned equidistant from said axis of the nozzle and uniformly distributed on a plane perpendicular thereto.

7. The cell-delivery unit of claim 2, wherein said patch-clamp electrode is a patch-clamp aperture in a partition.

8. The cell-delivery unit of claim 2, wherein said at least one sensing electrode disposed at a predetermined position on said nozzle comprises at least two electrodes positioned equidistant from said axis of the nozzle and uniformly distributed on a plane perpendicular thereto.

9. The cell-delivery unit of claim 1, further comprising:
    at least two distal positioning electrodes in the nozzle; and
    means for producing a first dielectrophoretic field using said distal positioning electrodes.

10. The cell-delivery unit of claim 9, further including:
    at least two proximal positioning electrodes above said distal positioning electrodes in the nozzle; and
    means for producing a second dielectrophoretic field using said proximal positioning electrodes.

11. The cell-delivery unit of claim 10, wherein said patch-clamp electrode is a patch-clamp aperture in a partition.

12. The cell-delivery unit of claim 10, wherein said at least one sensing electrode disposed at a predetermined position on said nozzle comprises at least two electrodes positioned equidistant from said axis of the nozzle and uniformly distributed on a plane perpendicular thereto.

13. The cell-delivery unit of claim 9, further including:
    at least two proximal positioning electrodes above said distal positioning electrodes in the nozzle; and
    means for producing a second dielectrophoretic field using said proximal positioning electrodes.

14. The cell-delivery unit of claim 1, wherein said at least one sensing electrode is disposed on a bottom surface of said nozzle, and wherein the unit further includes:
    at least two distal positioning electrodes in said nozzle; and
    means for producing a first dielectrophoretic field using said distal positioning electrodes.

15. The cell-delivery unit of claim 1, further including a cell sorter which incorporates a dielectrophoretic cage for controlling a release of test cells into said fluidic channel.

16. The cell-delivery unit of claim 1, wherein said patch-clamp electrode is a patch-clamp aperture in a partition.

17. The cell-delivery unit of claim 1, wherein said patch-clamp electrode is a patch-clamp pore in a pipette.

18. The cell-delivery unit of claim 1, wherein said at least one sensing electrode disposed at a predetermined position on said nozzle comprises at least two electrodes positioned equidistant from said axis of the nozzle and uniformly distributed on a plane perpendicular thereto.

19. A method for positioning a nozzle of a cell-delivery unit in alignment with a patch-clamp electrode structure, comprising the following steps:

producing an electric field emanating from said patch-clamp electrode structure;

detecting signals corresponding to said electric field using a sensing electrode disposed at a predetermined position with respect said nozzle; and positioning the nozzle so as to align an axis thereof with the patch-clamp electrode structure using said signals detected by the sensing electrode.

* * * * *